United States Patent
Das et al.

(10) Patent No.: US 8,532,744 B2
(45) Date of Patent: Sep. 10, 2013

(54) METHOD AND SYSTEM FOR DESIGN OF SPECTRAL FILTER TO CLASSIFY TISSUE AND MATERIAL FROM MULTI-ENERGY IMAGES

(75) Inventors: Bipul Das, Bangalore (IN); Ajay Narayanan, Bangalore (IN); Pratik Kamleshbhai Shah, Bangalore (IN)

(73) Assignee: General Electric Company, Niskayuna, NY (US)

( * ) Notice: Subject to any disclaimer, the term of this patent is extended or adjusted under 35 U.S.C. 154(b) by 124 days.

(21) Appl. No.: 13/215,634

(22) Filed: Aug. 23, 2011

(65) Prior Publication Data

US 2013/0053689 A1 Feb. 28, 2013

(51) Int. Cl.
*A61B 6/00* (2006.01)
(52) U.S. Cl.
USPC ................................. 600/425; 378/5
(58) Field of Classification Search
None
See application file for complete search history.

(56) References Cited

U.S. PATENT DOCUMENTS

| | | | |
|---|---|---|---|
| 6,950,492 B2 * | 9/2005 | Besson | 378/5 |
| 6,999,549 B2 | 2/2006 | Sabol et al. | |
| 7,319,733 B2 | 1/2008 | Price et al. | |
| 7,397,886 B2 | 7/2008 | Avinash et al. | |
| 7,583,779 B2 | 9/2009 | Tkaczyk et al. | |
| 7,801,271 B2 | 9/2010 | Gertner et al. | |
| 2006/0067473 A1 * | 3/2006 | Eberhard et al. | 378/98.9 |
| 2007/0133736 A1 * | 6/2007 | Chen et al. | 378/5 |
| 2008/0031507 A1 * | 2/2008 | Uppaluri et al. | 382/132 |
| 2009/0028287 A1 * | 1/2009 | Krauss et al. | 378/4 |

FOREIGN PATENT DOCUMENTS

WO 2010070554 A1 6/2010

OTHER PUBLICATIONS

Lell, Michael; Kramer, Manuel; Klotz, Ernst; Villablanca, Pablo; Ruehm, Stefan G.; Abstract : Carotid Computed Tomography Angiography With Automated Bone Suppression: A Comparative Study Between Dual Energy and Bone Subtraction Techniques; Jun. 2009—vol. 44—Issue 6—pp. 322-328.

Juergen Fornaro, Sebastian Leschka, Dennis Hibbeln, Anthony Butler, Nigel Anderson, Gregor Pache, Hans Scheffel, Simon Wildermuth, Hatem Alkadhi and Paul Stolzmann; Abstract : Dual- and multi-energy CT: approach to functional imaging; Insights Into Imaging; vol. 2, No. 2, 149-159.

Michael M. Lell, Fabian Hinkmann, Emeka Nkenke, Bernhard Schmidt, Peter Seidensticker, Willi A. Kalender, Michael Uder, Stephan Achenbach; Dual energy CTA of the supraaortic arteries: Technical improvements with a novel dual source CT system; European Journal of Radiology; 76 (2010) e6-e12.

* cited by examiner

*Primary Examiner* — Jacqueline Cheng
(74) *Attorney, Agent, or Firm* — Scott J. Asmus

(57) ABSTRACT

A method, system and apparatus for filtering multi-energy images using spectral filtering technique is described. In one embodiment, the method includes obtaining a first image of an anatomical object corresponding to a first radiation energy. In addition, the method includes obtaining at least one additional image, herein called a second image of the anatomical object corresponding to at least one second radiation energy. The at least one second radiation energy is distinct from the first radiation energy. The method also includes determining joint attenuation characteristics of each tissue at the first radiation energy and at the second radiation energy or their derivatives. The method also includes selectively filtering attenuation value in a multi-energy space due to at least one tissue to generate a filtered image from a reference image. The reference image is one of the first image or the second image or their derivatives.

17 Claims, 13 Drawing Sheets

METHOD AND SYSTEM FOR DESIGN OF SPECTRAL FILTER TO CLASSIFY TISSUE AND MATERIAL FROM MULTI-ENERGY IMAGES

BACKGROUND

The present application relates generally to medical image processing and, more particularly, to a method, system and apparatus for generating filtered images using spectral filtering technique for multi-energy images.

In a field of medicine, radiation based imaging devices such as a CT scanner may be used for deriving images of tissues of a patient. Single energy CT scanners project radiation of a single energy on the patient. Scanning data acquired from detectors coupled to the single energy CT scanner would be used for generating an image. The image would include representations of tissues based on attenuation properties of the tissues.

Segmentation of representations of tissues from the image is cumbersome due to overlap of attenuation properties of the tissues at any given energy. Several techniques have been proposed for segmentation of representations. These techniques separate the tissues based on appearance of shape and/or intensity of the tissues in a reference image. Consequently, these techniques are only applicable where such separability of structures is possible and do not work well in situations where two different types of tissues may share similar appearance.

Therefore, there is a need for a method and system for separating tissues in CT images in a more accurate manner.

BRIEF DESCRIPTION

The above and other drawbacks/deficiencies may be overcome or alleviated by embodiments of radiographic imaging presented herein. According to one embodiment, a method includes obtaining a first image of an anatomical object corresponding to a first radiation energy. The anatomical object comprises one or more tissues. In one example, the anatomical object may be a human patient. In addition, the method includes obtaining at least one additional image, herein called a second image of the anatomical object corresponding to at least one second radiation energy. The second radiation energy is distinct from the first radiation energy. The method also includes determining joint attenuation characteristics of each tissue at the first radiation energy and the second radiation energy or their derivatives. The method further includes selectively filtering attenuation value in the multi-energy space due to at least one tissue to generate an enhanced image from a reference image. The reference image is one of the first image or the second image or their derivates.

DRAWINGS

These and other features, aspects, and advantages of the present system and techniques will become better understood when the following detailed description is read with reference to the accompanying drawings in which like characters represent like parts throughout the drawings, wherein.

Figure 6:
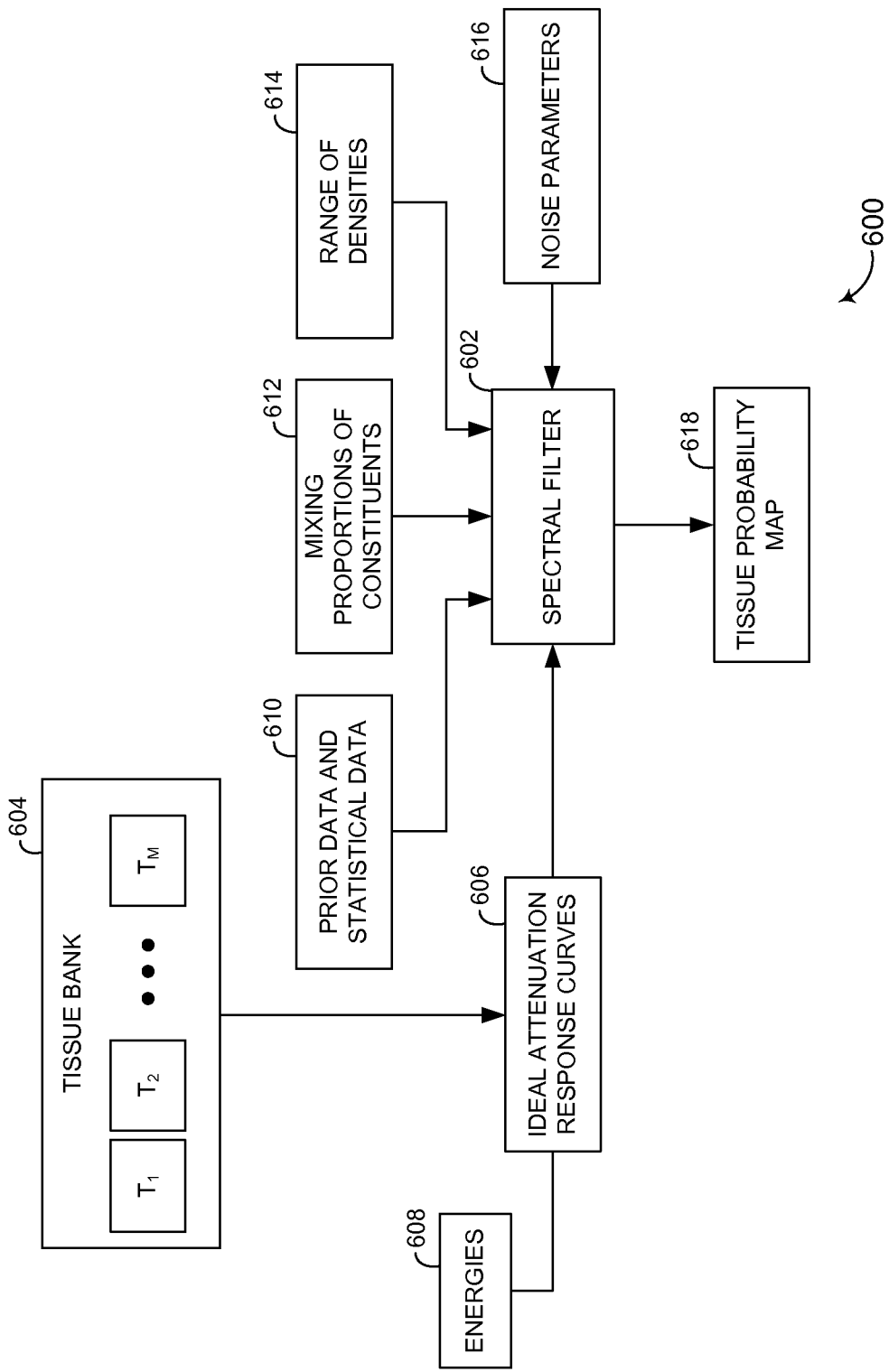
Figure 8A:
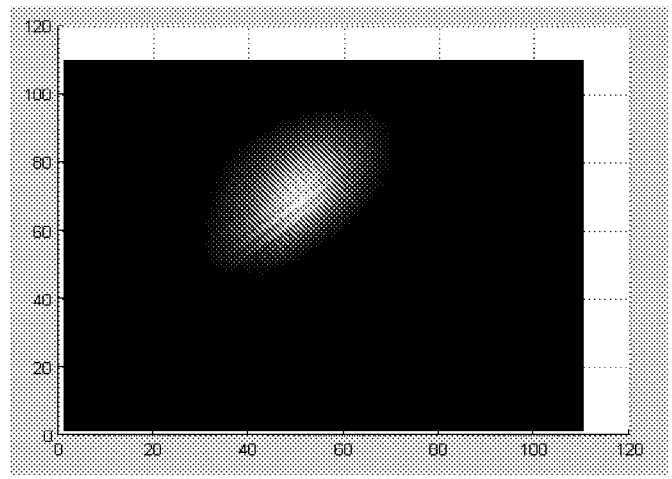
Figure 8B:
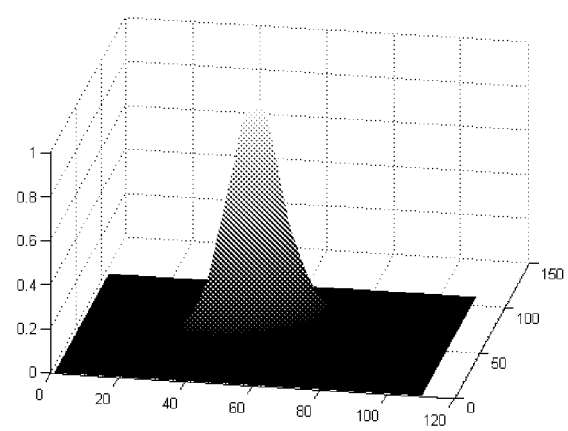
Figure 10:
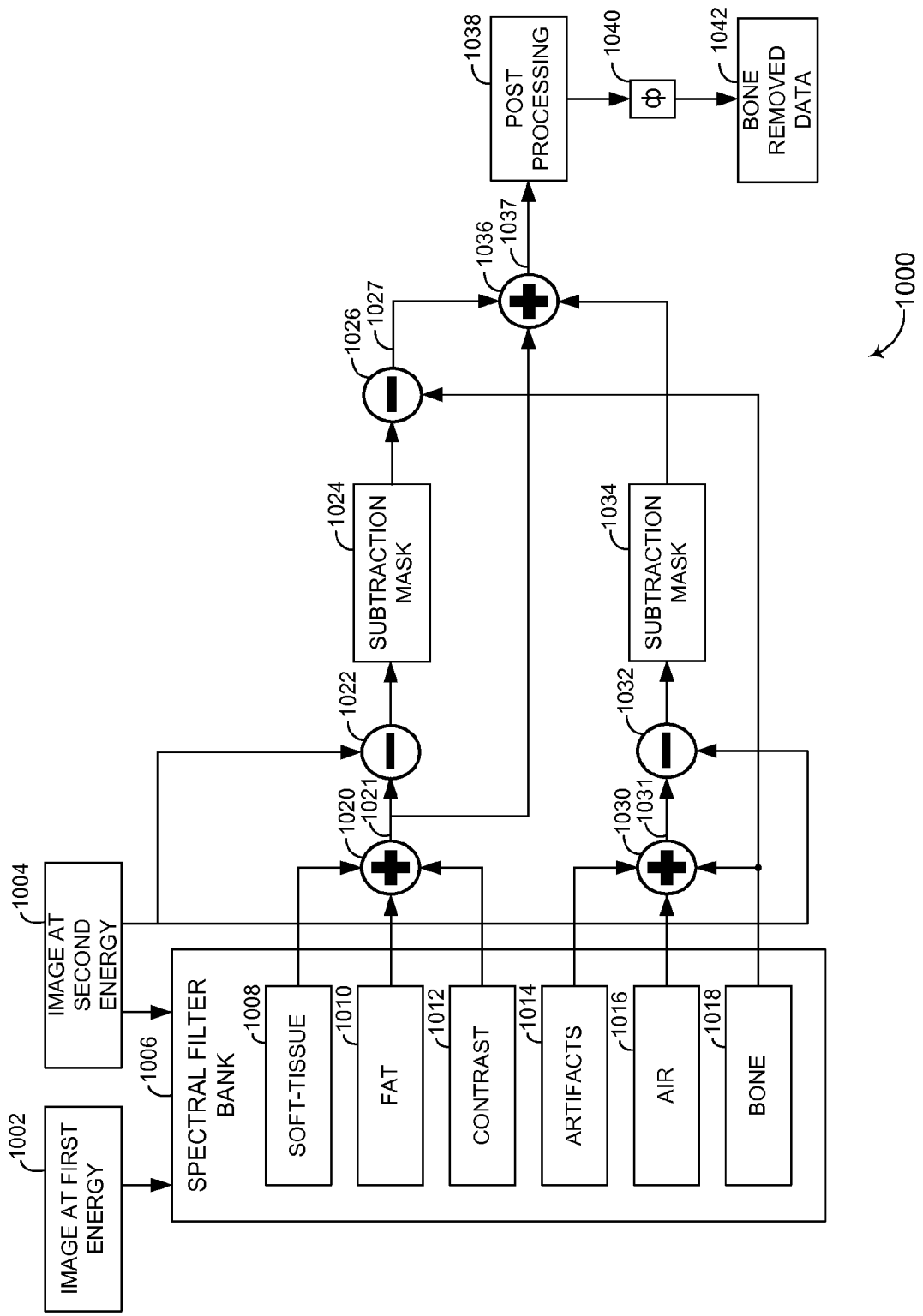
Figure 11:
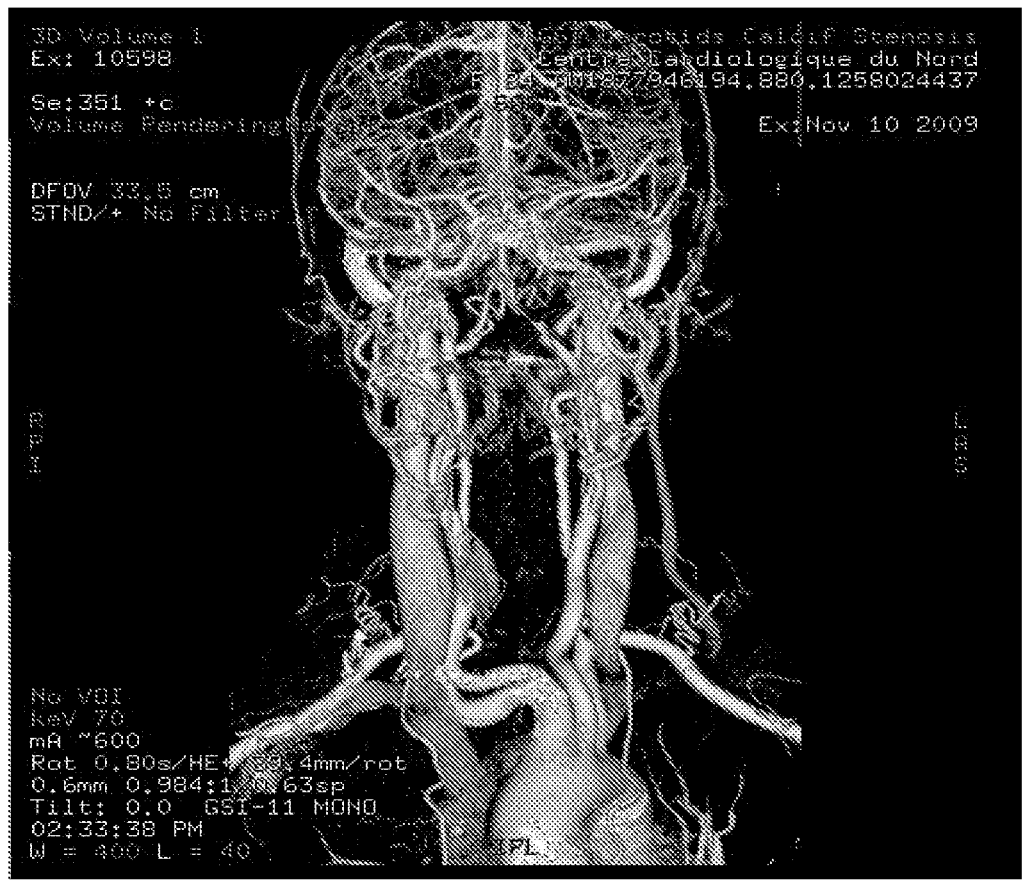
Figure 12:
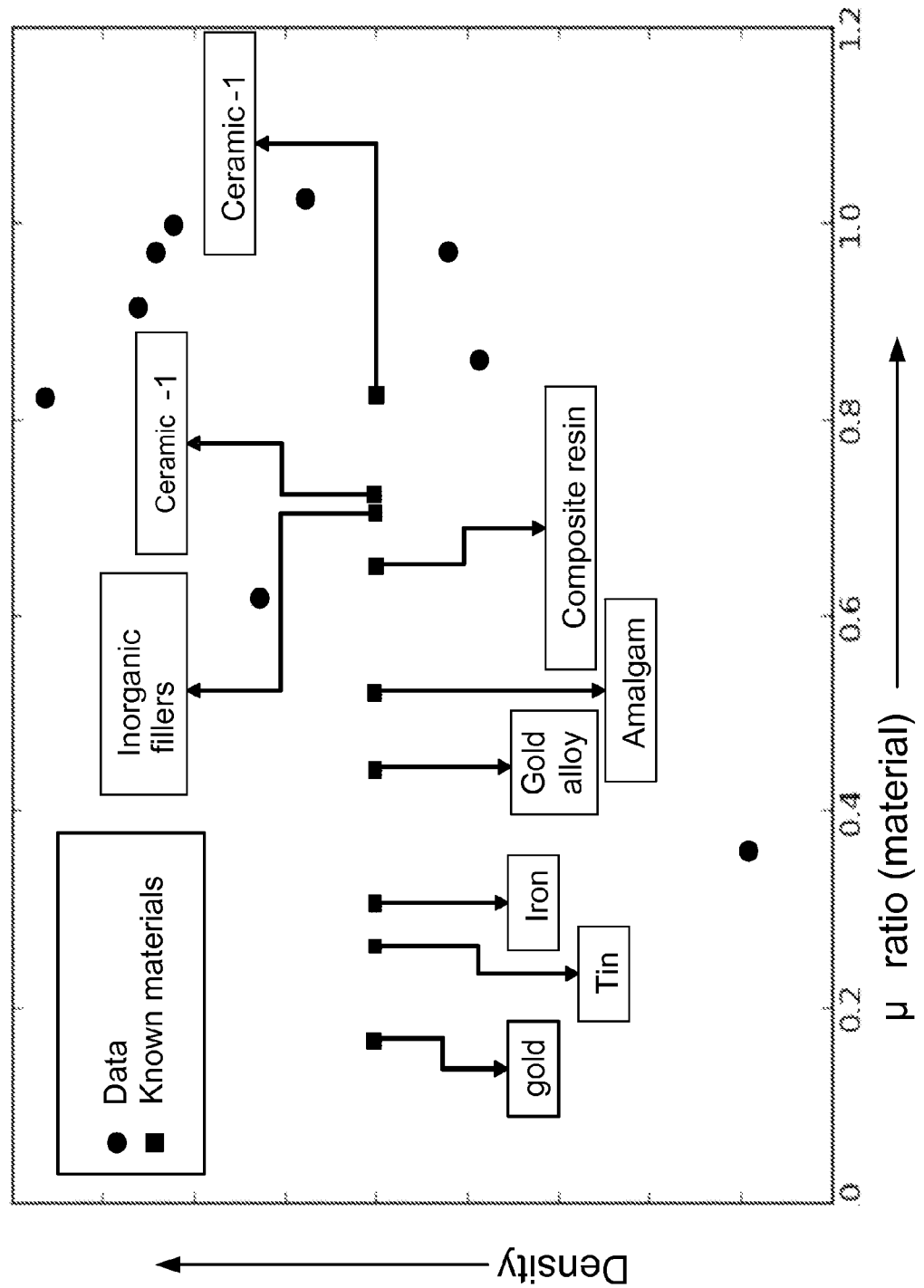

FIGS. 5A-F illustrate multiple examples of streak artifacts in a shoulder region, according to one embodiment;

FIG. 6 illustrates an exemplary high level architecture to design a spectral filter, according to one embodiment;

FIG. 7A-D are example result simulations illustrating probability distributions of a soft tissue, according to one embodiment;

FIG. 8A-B are representative response for a real data sample of the soft tissue, according to one embodiment;

FIG. 9A-D are example result simulations and real data illustrating representative distribution/response surface for a contrast enhanced blood tissue, according to one embodiment;

FIG. 10 illustrates a schematic diagram of an example system for bone removal from contrast enhanced CT angiography scans, according to one embodiment;

FIG. 11 illustrates an image comprising neuro-vascular tissues as a resultant of applying spectral filtering by modeling water rich, fat-rich and contrast tissues, according to one embodiment; and FIG. 12 illustrates a result of analysis of the material ratios and densities of known dental filling constituents and that of real data across subjects, according to one embodiment.

DETAILED DESCRIPTION

Figure 1:
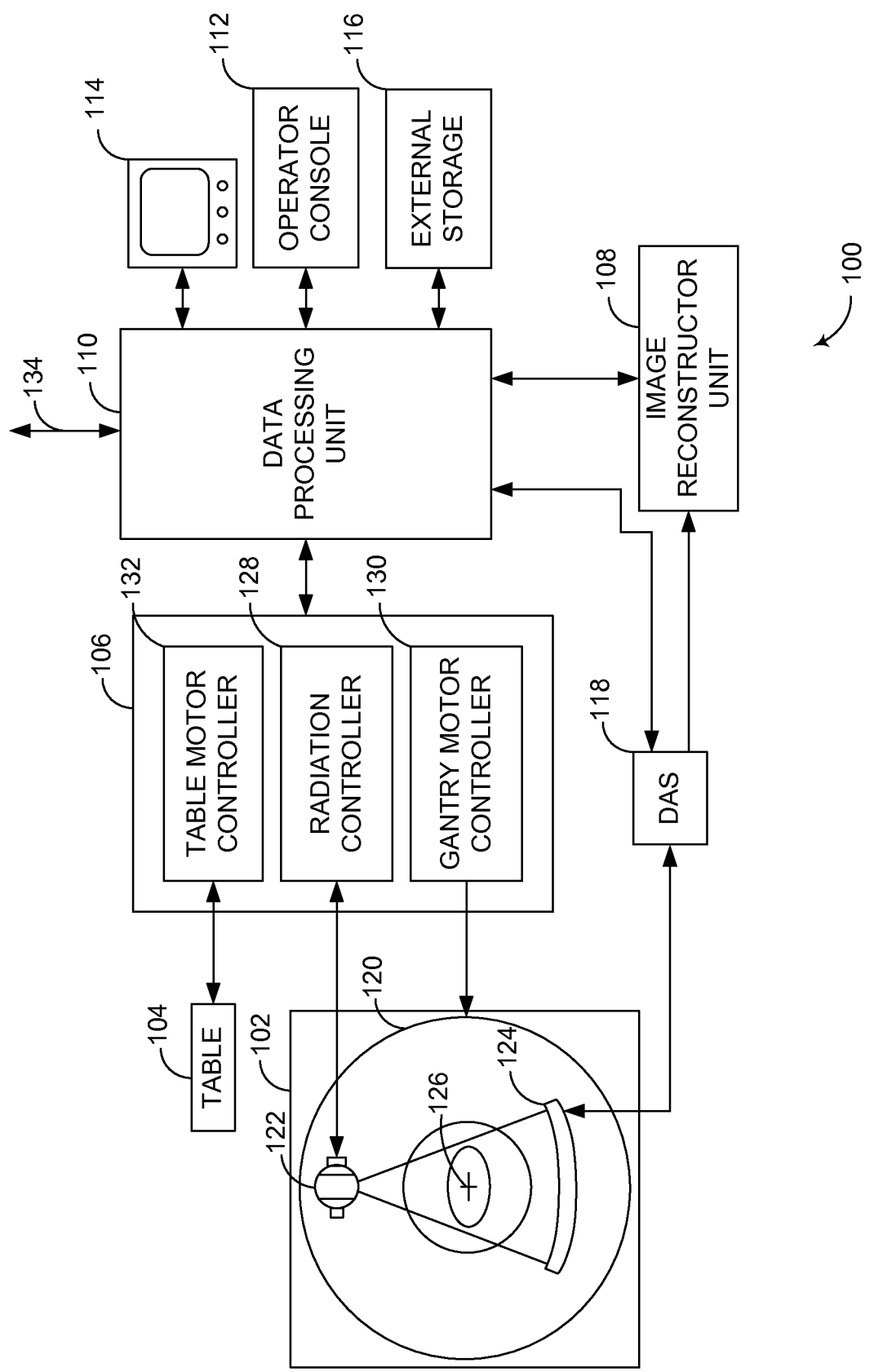
FIG. 1 is a schematic block diagram of CT based imaging system, according to one embodiment.

FIG. 1 is a schematic block diagram of Computed Tomography (CT) based imaging system, according to one embodiment. The CT based imaging system in this example includes, inter alia, a CT scanner 102, a table 104, a control system 106, an image reconstructor 108, a data processing unit 110, an operator console 112, an output interface 114, an external storage device 116 and a Data Acquisition System (DAS) 118. CT scanner 102 includes a gantry 120 in which a radiation source 122 and a radiation detector 124 are calculatively placed. The radiation source 122 may be an X-ray source, for example, used for generating x-rays at multiple energies. Radiation detector 124 may be an array of sensors which together sense a projected radiation that pass through an anatomical object (not shown). The sensors may be, for example, scintillators such as Cadmium Tungstate ($CdWO_4$). Radiation source 122 and radiation detector 124 are positioned at opposite ends in gantry 120 such that radiation detector 124 can receive the radiation emitted by radiation source 122.

Gantry 120 is also designed to allow table 104 to pass through a gap designed thereof. Position of table 104 is designed such that a center of rotation 126 of gantry 120 approximately coincides with any anatomical object placed on table 104 while passing through gantry 120. Control of gantry 120, radiation generation, and movement of table 104 are controlled through control system 106. Control system 106 includes a radiation controller 128, a gantry motor controller 130, and a table motor controller 132. Control system 106 receives inputs to control CT scanner 102 through data processing unit 110. Radiation controller 128 provides power, control signals, and timing signals to radiation source 122. Radiation controller 128 controls radiation source 122 through the control signals and the timing signals. Gantry motor controller 130 controls rotational speed and position of components in gantry 120. Table motor controller 132 controls movement of table 104 in coordination with gantry movement. Table motor controller 132 receives motor control signals from data processing unit 110.

Radiation source 122 and radiation detector 124 are rotated with gantry 120 within an imaging plane and around the anatomical object to be imaged such that the angle at which radiation intersects the anatomical object constantly changes. A group of radiation attenuation measurements, i.e., projection data, from radiation detector 124 at one gantry angle is referred to as a "view". A "scan" of the anatomical object comprises a set of views made at different gantry angles, or view angles, during one revolution of radiation source 122 and radiation detector 124.

Radiation source 122 can generate radiation at various energy levels. Radiation source 122 upon receiving control signals from radiation controller 128 generates radiation at a specific energy based on the control signals for a specific time intervals. The generated radiation is projected towards the anatomical object such as a patient. The radiation passes through the anatomical object being imaged. The radiation, after being attenuated by the anatomical object, impinges upon radiation detector 124. The intensity of the attenuated radiation received at radiation detector 124 is dependent upon the attenuation of the radiation by the anatomical object. Each sensor element of radiation detector 124 generates a separate electrical signal that is a measurement of the beam intensity at radiation detector 124 location. The intensity measurements from the sensors in radiation detectors 124 are acquired and processed to construct an image. The image is constructed based on the attenuation measurements from the scan which is processed to generate integers called "CT numbers" or "Hounsfield units" (HU), which are used to control the brightness of a corresponding pixel on a cathode ray tube display or an image. During a scan to acquire the radiation projection data, gantry 120 and the components mounted therein rotate about a center of rotation 24.

Also as used herein, the phrase "reconstructing an image" is not intended to exclude embodiments of the methods and systems described herein in which data representing an image is generated but a viewable image is not. However, many embodiments generate (or are configured to generate) at least one viewable image.

Rotation of components on gantry 120 and operation of radiation source 122 are governed by control system 106 of CT based imaging system 100. DAS 118 samples analog data from radiation detector 124 and converts the analog data to digital signals for subsequent processing. Image reconstructor unit 108 receives sampled and digitized radiation data from DAS 118 and performs image reconstruction (CT image). The reconstructed image is applied as an input to data processing unit 110, which stores the image in a storage device. Image reconstructor unit 108 can be specialized hardware or a computer programs executing on data processing unit 110.

Data processing unit 110 receives commands and scanning parameters from an operator via operator console 112 that may have a keyboard or speaker. Output interface 114 allows the operator to observe the reconstructed image and other data from data processing unit 110. In one embodiment, output interface 114 may include, but is not limited to, a cathode ray tube display, a Liquid Crystal Display (LCD), and a Light-Emitting Diode (LED) display. The operator supplied commands and parameters are used by data processing unit 110 to provide control signals and/or information to DAS 118, radiation controller 128, and gantry motor controller 130. In addition, data processing unit 110 controls table motor controller 132, which further controls a motorized table to position the anatomical object in gantry 120. Particularly, table 104 moves portions of the anatomical object through gantry 120 opening.

In one embodiment, data processing device 110 includes a reading medium, for example, a floppy disk drive, CD-ROM drive, DVD drive, magnetic optical disk (MOD) device drive, a Universal Serial Bus (USB) drive or any other digital device drive including a network connecting device such as an Ethernet device port for reading instructions and/or data from a computer-readable medium 52, such as a floppy disk, a CD-ROM, a DVD or any other digital source such as a network or the Internet, as well as yet to be developed digital devices. In another embodiment, data processing device 110 executes instructions stored in firmware (not shown).

Data processing unit 110 may be programmed to perform functions described herein, and as used herein, the term "data processing unit" is not limited to just those integrated circuits referred to in the art as computers, but broadly refers to computers, processors, microcontrollers, microcomputers, programmable logic controllers, Application Specific Integrated Circuits (ASIC), and other programmable circuits, and these terms are used interchangeably herein. Radiation based CT imaging system 100 is an energy-discriminating (also known as multi-energy) computed tomography system in that CT scanner 102 is configured to be responsive to different radiation spectra. This can be accomplished with CT scanner 102 to acquire projections sequentially at different x-ray tube potentials. For example, two scans are acquired either back to back or interleaved in which the tube operates at 70 kVp and 140 kVp potentials. An image corresponding to 70 kVp and another image corresponding to 140 kVp are generated based on the scans at corresponding energies. A person skilled in the art will appreciate that any other suitable potentials may also be used to scan the anatomical object. Further, more than two scans may also be performed at corresponding energies to obtain more than two images.

In one embodiment, data processing unit 110 processes the images generated at different energies in CT scanner 102. Each image includes representations of tissues, representations of artifacts, and partial volume effects. The images obtained are processed to identify each at least one tissue of one or more tissues in the anatomical object. Further, upon identification of the at least one tissue of the one or more tissues in the anatomical object, one or more tissues representations except a desired tissue representation may be selectively filtered through image processing in data processing unit 110 based on joint attenuation characteristics of corresponding tissues. In one embodiment, the filtering may be performed using one or more spectral filters designed for various tissues of a subject. After selective filtering process, an enhanced image is generated comprising a representation of the desired tissue. Alternatively, based on the joint attenuation characteristics determined for each tissues while at processing, a new image representing a selected one or more tissues can be generated. A process of generating an enhanced image based on joint attenuation characteristics is explained in FIG. 2. Although, data processing unit 110 is discussed in conjunction with radiation based CT imaging device 100 in FIG. 1, one skilled in art can appreciate that data processing unit 110 can be a standalone device capable of performing methods described herein.

Figure 2:
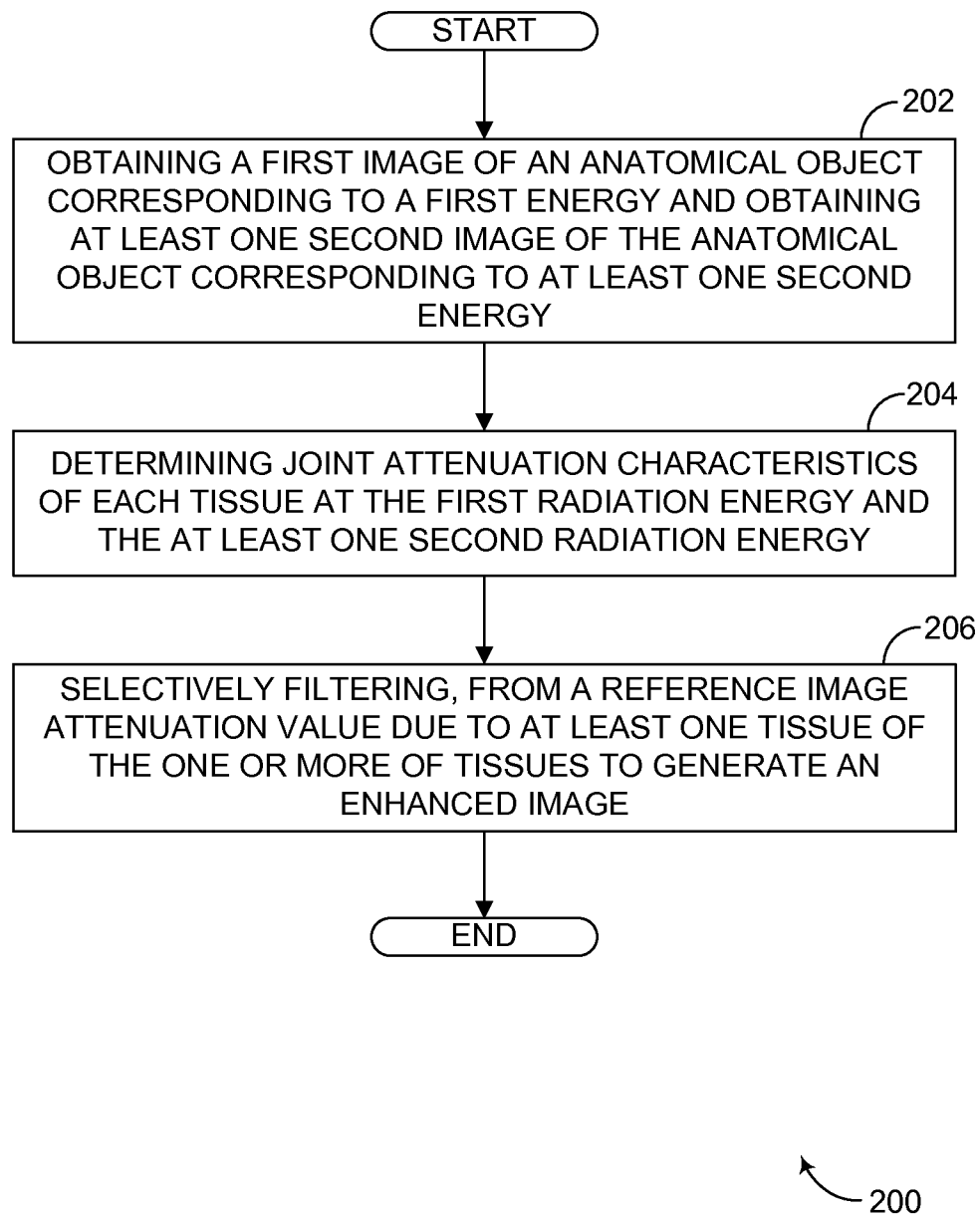
FIG. 2 is a flowchart illustrating an example process for generating a filtered image, according to one embodiment.

FIG. 2 is a flowchart illustrating an example process 200 for radiography based image processing, according to one embodiment. In step 202, a first image of an anatomical object, for example, a patient, corresponding to a first radiation energy is obtained. Also, at least one second image of the anatomical object corresponding to at least one second radiation energy is obtained. The first radiation energy and the at least one second radiation energy are distinct from each other. The anatomical object comprises one or more tissues.

Examples of the one or more tissues include, but are not limited to, soft tissues, bone tissues, blood (with and without contrast), fibrous tissues and fat.

In one embodiment, a plurality of CT scan images are obtained through the radiation based CT imaging system at two or more tube voltages. The plurality of CT scan images may then be converted into respective material basis pair images. Examples of the material basis pairs are, without limitation, iodine (water), calcium (iodine) and the like. Thereafter, the first image and the second image at the first radiation energy and the at least one second radiation energy, respectively, are obtained from the material basis pair images using a linear transform function, such as, for example, $$\mu(E)(x,y) = m1(x,y)\mu1(E) + m2(x,y)\mu2(E) \qquad (1)$$

where m1(x, y), m2(x, y), $\mu1(E)$ and $\mu2(E)$ represent image corresponding to a first basis material, image corresponding to a second basis material, known attenuation coefficients of the first and the second basis material, respectively.

The first image and the at least one second image may, for example, be generated by data processing unit 110. Alternatively, the first image and the at least one second image may be obtained through any other radiation based CT imaging system which is coupled to data processing unit 110 through a network connection 134. In yet another embodiment, data processing unit 110 can obtain the first image and at least one second image from a computer readable medium such as, but not limited to a CD, a DVD, a Blu-ray Disc (BD), a USB drive and the like.

Figure 3:
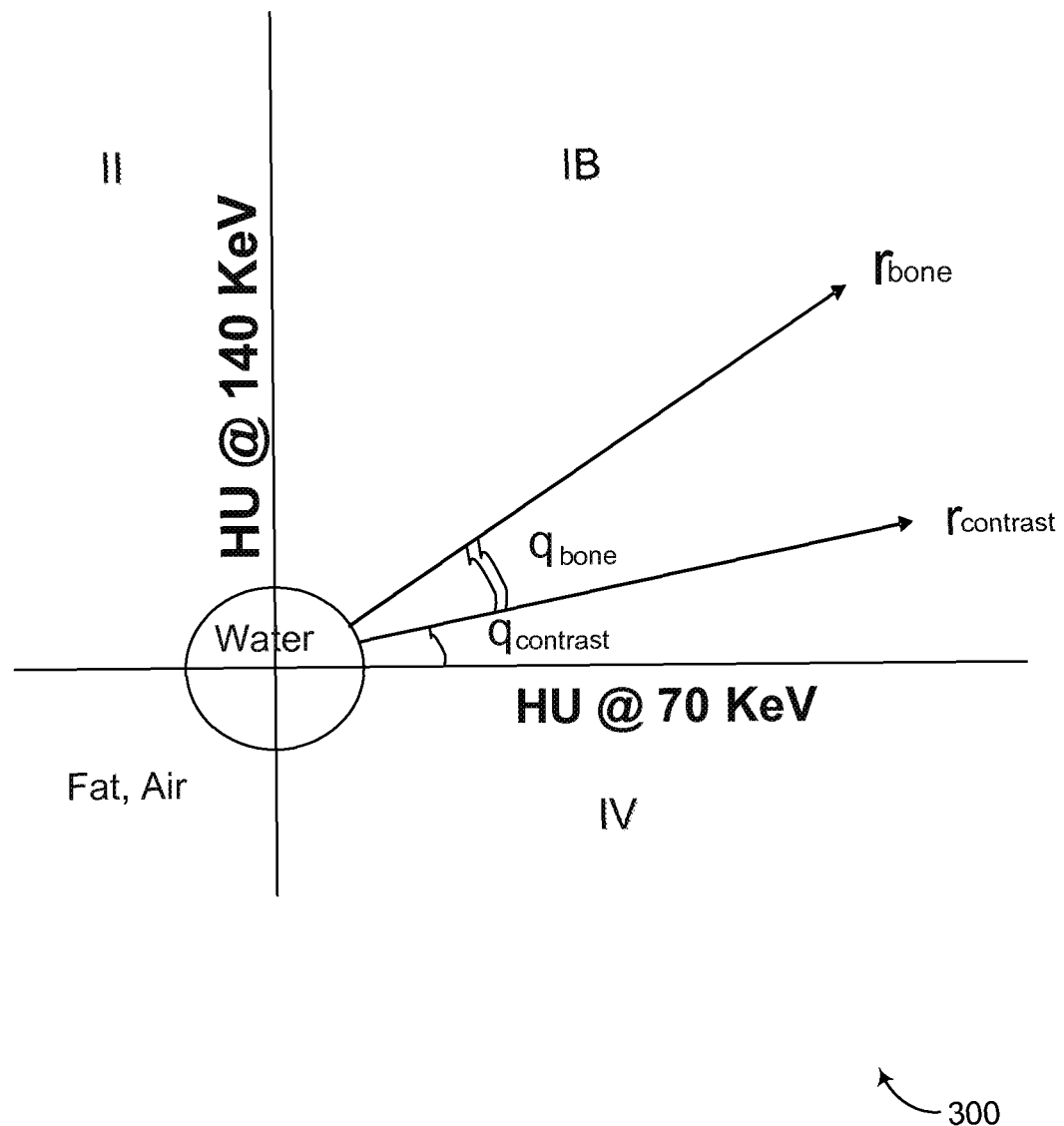
FIG. 3 illustrates an example of spectral map for two energies, according to one embodiment.

The first and the at least one second images are processed to generate a mutual information map. In one embodiment, the mutual information map is an information representing attenuation responses (in HU scale) of each of tissues for given radiation energies in a spectral map. The spectral map represents a multi dimensional graph with each axis representing attenuation values at different radiation energies. An example of the spectral map at two energies is illustrated in FIG. 3.

At step 204, joint attenuation characteristics of each tissue of the anatomical object are determined. In one embodiment, the joint attenuation characteristic for a given tissue is defined as a joint probability function. The joint probability function characterizes a response of the given tissue at the first and the at least second radiation energies in multi-energy space defined by the first and the at least one second radiation energies. The multi-energy space is hereinafter referred to as the Joint Attenuation Space. The joint probability function of a given tissue may be determined through at least one or combination of: (a) modeling the physics of X-ray attenuation of a given tissue (elemental, compound or a mixture model); (b) learning from prior data—the prior data include, but without limitation, anatomical priors, regional sampling, and responses of extracted tissues of multiple patient data; and/or (c) data driven statistical characterization of attenuation responses in the individual energy spaces.

A probability distribution in an attenuation space of a tissue '$t_1$' for given energy '$E_1$' is denoted by $p_{E_1}^{t_1}(x_{E_1})$. From spectral information, the joint attenuation response of the tissue '$t_1$' at the plurality of radiation energies can then be modeled as a joint probability distribution given by:

$$p_{E1,E2,\ldots En}^{t1}(x_{E1}, x_{E2}, \ldots, x_{En}) = p_{E1}^{t1}(x_{E1}) \cdot p_{E2/E1}^{t1}(x_{E2}|x_{E1}), \ldots p_{En/E1,E2,\ldots,En^{t1}}(x_{En}|x_{E1}, \ldots, x_{En-1}) \qquad (2);$$

where '$x_{Ei}$' is the response of the tissue '$t_1$' at a given radiation energy '$E_i$'. In one embodiment, the spectral information may be generated by observations of tissue attenuation characteristics from the prior data priors that include, but not limited to, anatomical priors, regional sampling, and prior responses of extracted tissues of multiple patient data.

In various embodiments, accuracy of the joint attenuation characteristics may be improved. In one embodiment, accuracy of the joint attenuation characteristics can be improved by building models of the one or more tissues. Each tissue may be considered as a mixture of different materials at different concentrations and is assumed to have varying density. Thus, in accordance with one embodiment, each tissue is modeled based on its material composition and/or density for calculation of the joint attenuation characteristics. For example, a bone tissue may be modeled based on material characteristics and/or density of the bone tissue.

In another embodiment, accuracy of the joint attenuation characteristics can be improved by using reference data derived (learning) from the prior data. The priors include, but are not limited to, data from anatomical priors, regional sampling values, responses of extracted tissues of multiple patient data. Given a known anatomical structure in an image, the anatomical prior may refer to the expected response/appearance in the vicinity of the known anatomical structure. Thus, in accordance with one embodiment, expectation of response/appearance in vicinity of standard response based on knowledge of given anatomical structure is considered for calculation of joint attenuation characteristics. Regional prior may include, but is not limited to, spatial variational analysis. In accordance with one embodiment, spatial variational analysis of responses may be considered for calculating joint attenuation characteristics Another prior could be driven by learning the joint spectral responses of one or more tissue types given that knowledge of the tissue labels are available in the image space.

In yet another embodiment, accuracy of the joint attenuation characteristics can be improved by data driven statistical characterization of attenuation responses in the individual energy spaces. In data driven statistical characterization method, analysis of images in the individual energy spaces are performed and the information obtained from the analysis thereof is combined in the joint attenuation space. Thus, statistical characterization method may be used for calculating joint attenuation characteristics.

Thereafter, in step 206, attenuation value contributions of at least one tissue of the one or more tissues can be selectively filtered from a reference image to generate a filtered image. Any of the first image and the at least one second image, or their derivatives may be used as the reference image. One or more spectral filters may be designed such that the filtered image includes an anatomical representation of one or more desired tissues. Various embodiments of the general design of a spectral filter with its boundary conditions are now described in subsequent paragraphs.

Given a multi-energy acquisition with measurements performed at 'n' distinct energies. Then, the Joint Attenuation Space 'J' spanned by these energies may belong to the n-dimensional space of real numbers '$R^n$'. Given a tissue, a spectral filter design implies defining the boundary conditions of a sub-space S∈J, such that the probability of occurrence of the given tissue is maximized in this sub-space 'S'.

Every point in space 'J' is a projection of the attenuation response of a physical point across multiple energies as measured by CT system 100. Origin of the space 'J' comprises of the joint response of pure water across the 'n' energies. A material (elemental/compound) of known density maps onto a fixed point in 'J'. Response at this point is given by the linear attenuation coefficient k (E1 ... En)=$\mu$(E1 ... En)×$\rho$, where '$\mu$' is the mass attenuation coefficient for a given material at a given energy and 'ρ' is the density. Variation in density ρ may lead to a line response in the space 'J'. The limits of the line may be given by lowest and highest values of the density of the material in the tissue that are possible in an anatomical object. A tissue may be comprised of one or more pure materials, or a mixture of materials. The mixture response maps to a point cloud in 'J' whose bounds are set by the density ranges and the mixing proportions of the materials.

Boundary condition of a mixture of tissues may be defined based on the mixing proportion limits of constituent materials and their range of densities. For example, boundary condition for a mixture involving blood and contrast agent may be defined based on the mixing proportion limits of the contrast agent and the contrast agent density. In one example, considering a case of iodinated contrast agent mixed in blood, a design of the boundary conditions for such as case may be based on the following analysis. Assuming that 100 ml of iodinated contrast agent having known density and known chemical composition is injected in 5000 ml of blood (average blood amount in human body). If the iodinated contrast agent is diluted in entire blood volume, the contrast to blood volume ratio becomes 100:5000 (i.e., 1:50). If the scan is performed before the contrast agent gets diluted to entire blood volume, the ratio may increase from 1:50 and could be as much as 1:1 or higher (e.g., in contrast pooling situations). Both extremes of mixing may reduce a clinical usability of the scan data. While ratios greater than 1:20 reduce the iodinated contrast agent signal, ratios lower than 1:10 cause blooming and pooling artifact due to strong (iodinated) contrast agent signal. A spectral filter (e.g., pass-band) may now be designed to cover a specific range, for example, practically usable ratio limits such as, 1:10-1:20 or may pass the whole range of possible ratios from 1:0 to 0:1. Selection of these ranges is referred to as setting the 'boundary conditions'.

The method described herein is applicable for a variety of applications. In one example implementation, a design of sub-space 'S' over a dual-energy space 'J' is illustrated. FIG. 3 illustrates an example of spectral map 300 for two energies, according to one embodiment. CT scan images may be obtained for two energies. Obtained CT scan images may be decomposed using, for example, Iodine (water) as the material basis pair. Monochromatic images may be generated at, for example, 70 keV (i.e. the first image) and 140 keV (i.e. the second image) using the material basis pair. A mutual information map may be generated in a spectral map 300 using attenuation responses of various tissues obtained from the first image and the second image that are mapped into the spectral map 300. The spectral map is comprised of two axes, each axis in spectral map 300 may be designated for a particular radiation energy representing attenuation values corresponding to the radiation energy. For example, x-axis may be designated for representing attenuation values at radiation energy 70 keV, and y-axis may be designated for representing attenuation values at radiation energy 140 keV, as illustrated in FIG. 3, though a person skilled in the art will appreciate that the order of the axes can be easily reversed. The monochromatic images define the bounds of the space 'J' in current example.

In current example, attenuation distribution of any tissue in the spectral map for the two radiation energies may be defined by:

$$r(E_1;E_2) = \sqrt{a^2+b^2};$$

$$\theta(E_1;E_2) = \tan^{-1}\frac{b}{a};$$

where $a = \sum_{j=0}^{N} \alpha_j \mu_j(E_1)\rho_j \ \mu_w(E_1);$ and $b = \sum_{j=0}^{N} \alpha_j \mu_j(E_2)\rho_j - \mu_w(E_2);$ where $\mu_j(E_i)$ are the attenuation coefficients of the materials in joint attenuation space 'J' at energies '$E_i$'; $\alpha_j$ is the mixing proportions of the material in the tissue and '$\rho_j$' is the density of the material; and '$\mu_w(E_i)$' is the attenuation of pure water for the energy '$E_i$'.

Using National Institute of Standards and Technology (NIST) values for mass attenuation of different materials at the given energy values, any tissue may be modeled as a mixture of those materials. As described above, the boundary conditions may be determined by the possible mixing proportions and the possible range of densities of the materials in the tissue. In one example implementation, bone can be modeled as a mixture of calcium-hydroxyapatite, blood and fat at varying proportions and densities. Subspace 'S' for a given tissue can be represented in joint attenuation space 'J' as a function of 'r' and 'θ'. Spectral filtering for any possible human tissue or material mixture may be designed using aforementioned method, satisfying all the boundary conditions, including but not limited to normal tissues, pathologically altered tissues, and the like.

Practical systems may have noise, which impacts the tissue characteristics in the joint attenuation space and causes spread of the tissue response. Noise in the image can potentially manifest due to detector noise, reconstruction filter, photon starvation etc. Noise in the image may be suitably incorporated into the design of the filter. CT noise characteristic may be a function of the energy $E_i$. Thus, the modified equation can be expressed as:

$$a = \sum_{j=0}^{N} \alpha_j \mu_j(E_1)\rho_j - \mu_w(E_1) + n(E_1);$$

$$b = \sum_{j=0}^{N} \alpha_j \mu_j(E_2)\rho_j - \mu_w(E_2) + n(E_2);$$

where $n(E_i)$ is the noise at a given energy $E_i$.

Figure 4:
FIG. 4 is an image generated using a spectral information of artifacts, partial volume effects and regions not modeled as tissues, according to one embodiment.

While sub-space 'S' can be modeled for all tissues that exists in an anatomical object, there are regions in the joint attenuation space 'J' which do not belong to any tissue response. Let the region be denoted as 'A∈J', such that A∩($U_j$S)=φ, where '$U_j$S' is the union of the space covering all the tissues in a human system. The region 'A' comprises the system related artifacts and partial volume effects compounded together. The spectral space for this region cannot typically be modeled by any combination of known materials. An example of artifacts, partial volume effects, and other elements detection using the spectral information is illustrated in FIG. 4, where regions not modeled as tissues are captured.

Figure 5A:
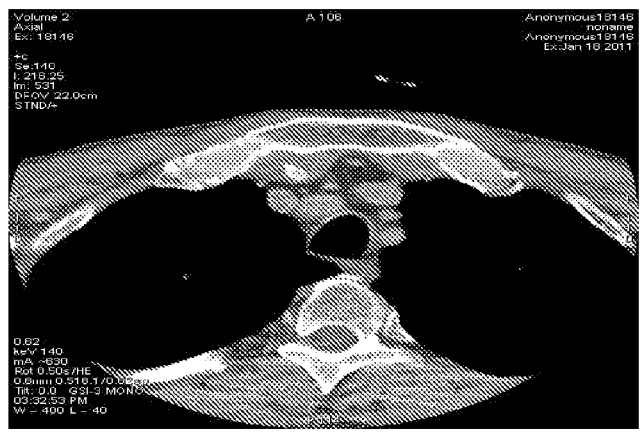
Figure 5B:
Figure 5C:
Figure 5D:
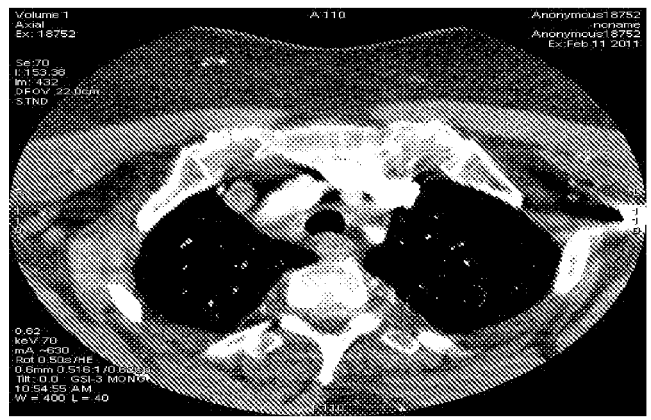
Figure 5E:
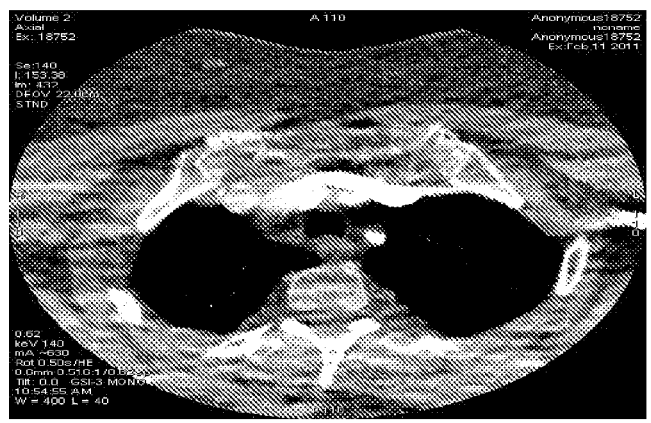
Figure 5F:

Extreme conditions that may potentially occur due to, without limitation, acquisition or reconstruction errors at one and/or multiple energies can also be modeled as described in the aforementioned method. An example of the extreme condition includes streak artifacts. Streak artifacts in the image may be defined as regions in the image where high X-ray attenuation along a path leads to false alternate enhancement and reduction of signals in the image. This false alternate enhancement and reduction of signal are an energy dependant phenomenon. Consequently, the manifestations of these artifacts across energies may be different. This spectral variational signature of the manifestations of the artifacts can be analyzed to lead up to detection of pixels that are affected by artifacts versus those that are not. This is illustrated in FIG. 5 across two cases with varying levels of streak artifact in the shoulder region. FIG. 5A and FIG. 5B show example monochromatic images at two energies having low extreme conditions, whereas monochromatic images having high extreme conditions are illustrated in FIG. 5D and FIG. 5E. The spectrally affected pixels from these images are detected, as illustrated in FIG. 5C and FIG. 5F, respectively for the example scenario.

An exemplary high level architecture 600 to design a spectral filter 602 is shown in FIG. 6. Design of spectral filter 602 for any given tissue is explained below with representative examples. Spectral filter 602 may be designed based on data associated with a tissue of interest ($T_N$). The data as described herein may include ideal X-ray attenuation responses 606 of constituents of $T_N$ at various energies 608, prior data and statistical information of attenuation responses in the individual energy spaces 610, mixing proportions 612 of the tissue constituents, and/or density range values 614 for each tissue constituents.

Figure 7A:
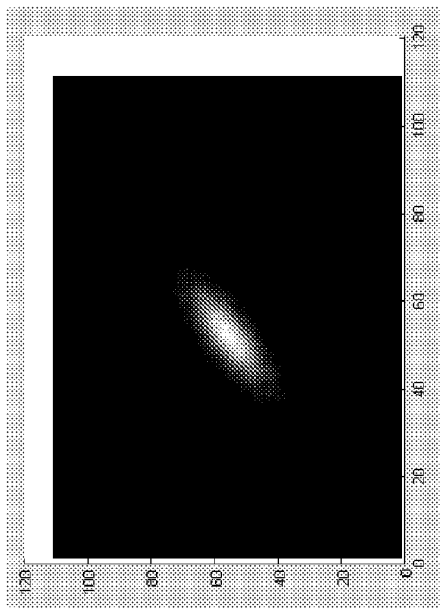
Figure 7B:
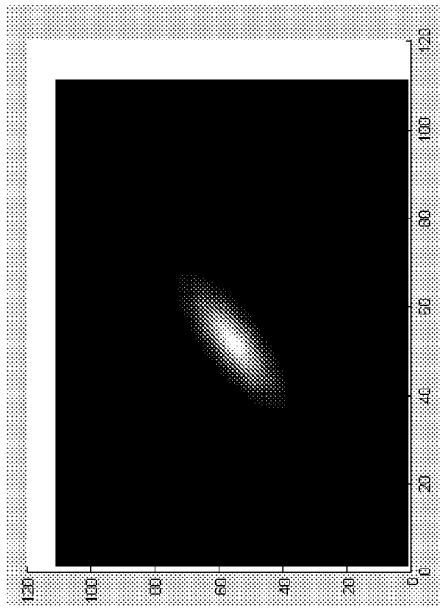
Figure 7C:
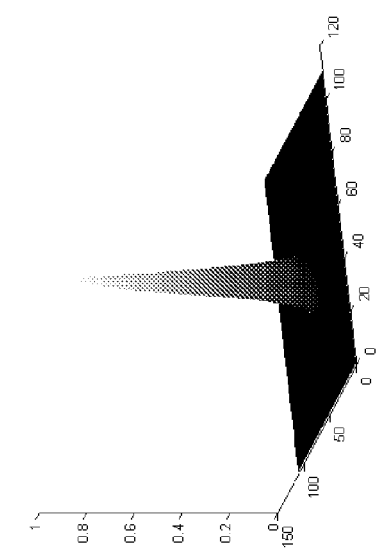
Figure 7D:
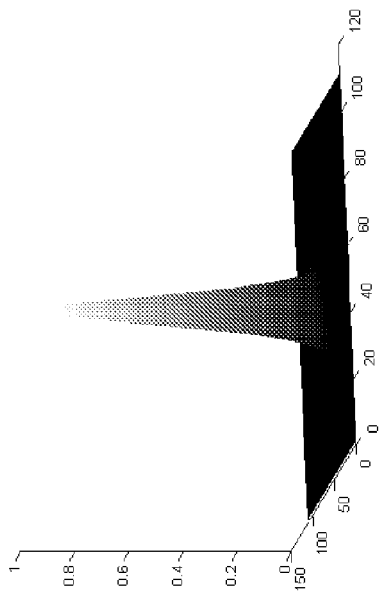

Tissue constituent information may be obtained from tissue bank 604. Further, (ideal) X-ray response curve(s) 606 for each of the constituents at various energies may be calculated. Using X-ray response curve(s) 606 of the tissue constituents and the range of densities 614 for each constituent, attenuation values may be generated across the range of mixing proportions of the constituents of the tissue. Further, a joint probability density function may be generated at multiple energies 608 by random sampling of tissue mixtures/densities within the parametric range. Furthermore, numerical sampling may be used to factor in system noise parameters 616 as a zero-mean additive Gaussian with a sigma as one of the input parameters. Using the data associated with a tissue of interest $T_N$ (e.g., 606, 610-614), and/or noise parameters 616, a joint probability distribution for the tissue $T_N$ in the space 'J' may be determined. Spectral filter 602 may then be designed to maximize the joint probability density function within appropriate boundary conditions. Output of spectral filter 602 may be a joint probability map 618 indicating the probability of occurrence of the tissue $T_N$ in the joint attenuation space 'J'. In one example implementation, the joint probability map may be modeled using simulation on the random samples. Systematic bias in measurement may be also captured as an offset to the experimental x-ray response curves. Results of one such simulation on $5 \times 10^4$ and $5 \times 10^5$ samples for soft-tissue filter design are shown as probability distributions in FIG. 7A and FIG. 7B, respectively. FIG. 7C and FIG. 7D depict the response surface of the simulation corresponding to the distributions in FIG. 7A and FIG. 7B, respectively. For the sake of comparison, a representative distribution/response surface for a real data sample of the tissue $T_N$ (e.g., soft tissue) is illustrated in FIG. 8A and FIG. 8B, respectively.

Various parameters for designing the spectral filter may be selected based upon, for example, the type of tissue for which the spectral filter is to be designed. For example, while designing a spectral filter for a soft-tissue at energy values 70 keV and 140 keV, following exemplary parameters may be used. Mean value of density range of the soft-tissue equal to 1.03 g/cc (with standard deviation of 0.005). The system noise parameters are set as $4 \times 10^{-7}$ cm$^2$/g at 70 keV and $1 \times 10^{-7}$ cm$^2$/g at 140 keV. Further, the ideal attenuation response curves for the constituents of the desired soft tissue may be obtained from an ICRP database named "brain".

Figure 9B:
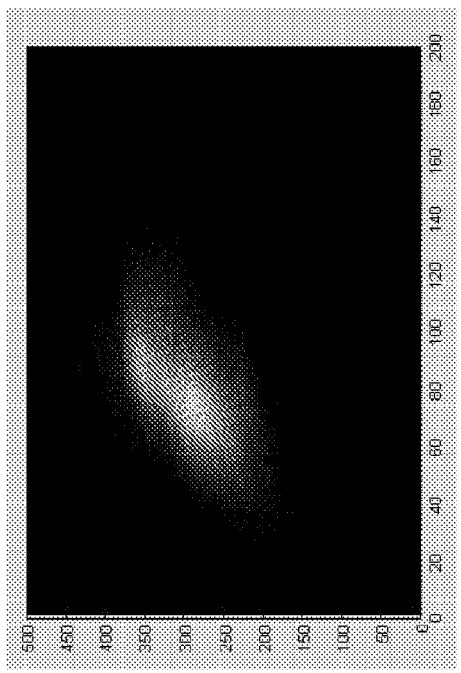
Figure 9A:
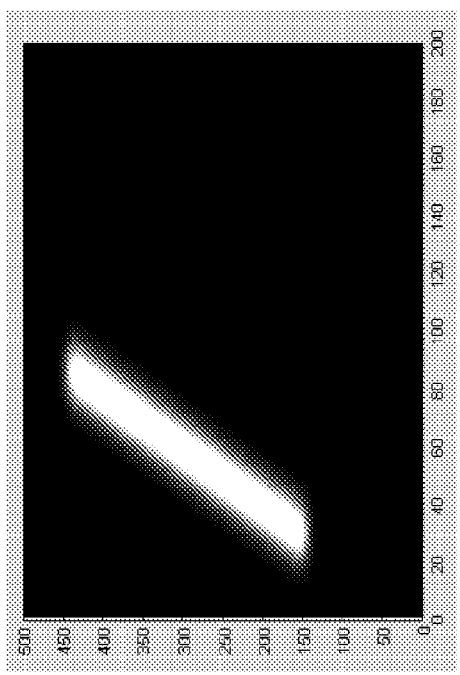
Figure 9D:
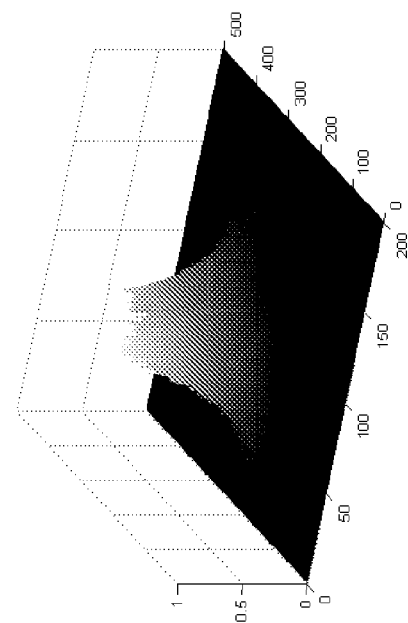
Figure 9C:
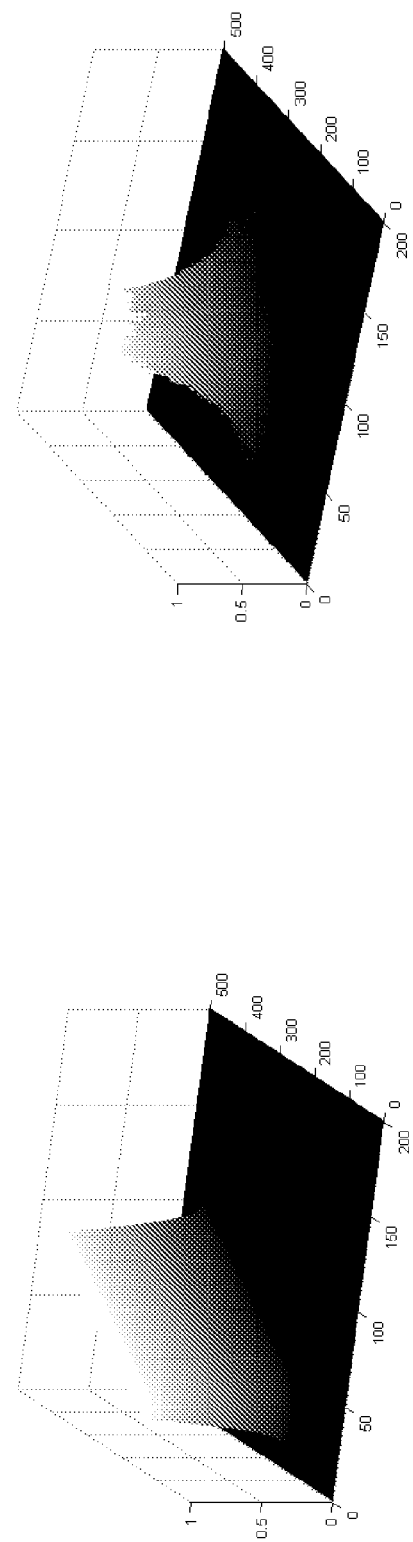

In another example, following considerations may be made for design of spectral filter for a contrast agent mixed blood. In the example, spectral filter for generating a probability map in the joint attenuation space 'J' is designed based on mixing proportions of blood and contrast agent. While the individual responses for each constituent (blood, contrast agent) may be well bounded, the response of the mixture is a function of the mixing proportions. The spectral filter design may model the maximum probability of finding any mixture within the proportion bounds on a line joining the two constituents. An example of which is depicted in FIG. 9. FIG. 9A and FIG. 9C depict simulation results with $5 \times 10^5$ points as a distribution/surface for contrast enhanced blood. In practice, dominant mixing proportion(s) may tend to manifest as peaks on selective points on a line. One example of this effect is shown in FIG. 9B and FIG. 9D.

In current example, the constituents for the contrast agent mixed blood are taken as blood and contrast. Further, for a design of a spectral filter for contrast agent mixed blood at energy values 70 keV and 140 keV, following exemplary parameters may be used. Range of mixing proportions of the blood and the contrast agent considered to be [0, 1]. Range of mixing [0, 1] implies that the mixture could span from being pure blood (bound=0) to pure contrast (bound=1) and all other mixing proportions in between them. Mean value of density range equal to 1.06 (g/cc) for the blood and 1.349 g/cc for contrast agent. The noise parameters are set as $1.62 \times 10^{-2}$ cm$^2$/g at 70 keV and $2.6 \times 10^{-3}$ cm2/g for 140 keV based on system. The ideal attenuation response curves for the blood may be obtained from ICRU database. The ideal attenuation response curves for the contrast agent are obtained from GE Healthcare data sheets.

Although, spectral filtering design is described for soft tissues and blood-contrast mixture as examples, one skilled in the art can appreciate that the method can be used to model tissues with higher number of constituents (for example, bone tissue), varying ranges of mixing proportions, varying ranges of densities of constituents to compute the probability of occurrence of corresponding tissue in the space 'J' within appropriate boundary conditions. An example of usage of the method for removal of bone representations from an image is described in FIG. 10.

FIG. 10 illustrates a schematic diagram of an example system 1000 for bone removal from contrast enhanced CT angiography scans, in accordance with one embodiment. In current example, a first image 1002 at first radiation energy and a second image 1004 at second radiation energy may be obtained. Images 1002 and 1004 may be used to generate a spectral filter bank 1006 comprising spectral filters 1008-1018 corresponding to multiple tissues. An example of spectral filter bank 1006 is illustrated in system 1000.

Probability maps generated for soft-tissue, fat and contrast from corresponding spectral filters 1008, 1010, and 1012, respectively may be added. The addition operation is illustrated by block 1020. It will be appreciated that the additions and subtraction described in this example represent unions and exclusions, respectively and not arithmetic additions/subtraction. The result of the addition is illustrated by a signal 1021. Signal 1021 may be a probability map providing maximum probability of occurrence of soft-tissue, fat and contrast in a sub-space 'S'. Further, signal 1021 may be subtracted from image 1004, in one example implementation. The subtraction operation is illustrated by block 1022. In current embodiment, the resulting image is used as a subtraction mask. The result of subtraction is shown as subtraction mask 1024 block. Further, probability map of bone obtained from spectral filter 1018 may also be subtracted from subtraction mask 1024. The subtraction operation is illustrated as 1026. Result of subtraction 1026 (depicted by signal 1027) may correspond to an image without representations of soft-tissue, fat, contrast and bone.

Similarly, probability maps generated for artifacts, air and bone from corresponding spectral filters 1014, 1016, and 1018, respectively, may be added. The addition operation is illustrated by block 1030. The result of the addition is illustrated by a signal 1031. Signal 1031 may be a probability map providing maximum probability of occurrence of artifacts, air and bone in a sub-space 'S'. Signal 1031 may be subtracted from image 1004, in current example implementation. The subtraction operation is illustrated by block 1032. In current embodiment, the resulting image is used as subtraction mask.

Further, signal 1027, signal 1021, and signal 1034 may be added. The addition operation is illustrated by block 1036. The result of addition 1036 is illustrated by signal 1037. Signal 1037 may be an image without bone representations. The signal 1037 may be post processed to remove noise in a resultant image. The post processing operation is illustrated by block 1038. Optionally, traditional or known methods of image processing may be performed on the resultant image to further enhance the quality of the image. The optional image processing operation is illustrated by block 1040 (depicted by symbol '¢'). The image processing operations may be a distance based morphological operations and/or feature analysis on connected components. The morphological operations may include, but are not limited to, dilation, erosion, opening, and closing. The feature analysis may include geometric feature analysis and/or intensity feature analysis. The geometric features may include size, eigen based shape metrics, tubularity measures, and the like. The intensity features may include texture features, spectral signal statistics, image gradients, and the like. Although, optional image processing block 1040 is illustrated after post processing block 1038, one skilled in art can appreciate that optional image processing block 1040 can be placed anywhere in the system 1000 for performing image processing operations. The result of post processing may be an enhanced image 1042 without bone representations. An example image 1100 without representations of bone is illustrated in FIG. 11.

The foregoing represents only one example processing performed to remove bone tissues. A person skilled in the art will appreciate that other variations may suitably be employed. For example, image 1002 may be used instead of image 1004 for producing the final output image. Further, though the example combines soft-tissue, fat and contrast in one processing path and bone, artifact and air in a second processing path, it need not be so. Any other suitable processing combination may be used.

The spectral filtering presented herein may also be applied for in-vivo detection and characterization of foreign bodies. These could be analysis of implanted joint prosthesis, stents, pacemakers, dental fillings, shrapnel, projectiles, etc. There are numerous clinical benefits and applications of such characterizations. Knowledge of material constituents may aid in decisions relating to MRI compatibility, improved shimming, imaging around metals, better management of specific absorption rates for tissues and assessment of biocompatibility issues in cases of restenosis in a stented vessel, etc. As an illustrative example, analysis of multiple datasets corresponding to neurovascular imaging of the head and the constituents of dental fillings was performed. The ratio of the linear attenuation coefficients of different fillings across two energies –140 keV and 70 keV was computed. Two fillings containing the same material may give rise to similar ratios accounting for variations due to system noise. FIG. 12 shows the material ratios of known dental filling constituents and that of measured data points across multiple subjects. The result of the analysis (as depicted in FIG. 12 for one example scenario) may be used to detect, differentiate and/or characterize multiple materials that constitute some of the major classes of dental fillings materials generally used in practice.

Depending on application requirements, aforementioned spectral filtering technique can be used in conjunction with other known state-of-art image/signal analysis methods. For example, the spectral filtering can be used for tissue classification, segmentation and analysis and can be precursor to tissue labeling. The spectral information modeling can also be used to enhance image quality both in the image domain as well as in projection space in the reconstruction chain.

The methods disclosed herein can be embodied in the form of computer or controller implemented processes and apparatuses for practicing these processes. These methods can also be embodied in the form of computer program code containing instructions embodied in tangible media, such as floppy diskettes, CD-ROMs, hard drives, and the like, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

While the application has been described in considerable detail with reference to a few exemplary embodiments only, it will be appreciated that it is not intended to limit the application to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

What is claimed is:

1. A method comprising:
   obtaining a first image of an anatomical object corresponding to a first radiation energy, wherein the anatomical object comprises one or more tissues;
   obtaining at least one second image of the anatomical object corresponding to at least one second radiation energy, wherein the at least one second radiation energy is distinct from the first radiation energy;
   determining joint attenuation characteristics of each tissue at the first radiation energy and the at least one second radiation energy;
   designing a spectral filter for at least one desired tissue from the one or more tissues based at least in part on the joint attenuation characteristics and a mixing proportion of a plurality of constituents of the at least one desired tissue; and selectively filtering using the spectral filter, attenuation values due to the at least one desired tissue from a reference image to generate an enhanced image, wherein the reference image is one of the first image or the at least one second image.

2. The method of claim 1, further comprising generating a mutual information map between the first image and the at least one second image based on attenuation values of voxels in the first image and attenuation values of corresponding voxels in the at least one second image.

3. The method of claim 2, further comprising filtering one or more artifacts from the first image and the at least one second image based, at least in part, on the mutual information map.

4. The method of claim 1, wherein the one or more tissues comprise at least one of a bone tissue, a vascular tissue, blood, and a soft tissue, fat, fibrosis and necrotic tissue.

5. The method of claim 1, wherein determining joint attenuation characteristics of each tissue comprises computing joint probability density of attenuation response of the each tissue at the first radiation energy and the at least one second radiation energy.

6. The method of claim 1, wherein determining joint attenuation characteristics of each tissue comprises computing the joint attenuation characteristics of the each tissue based, at least in part, on a model of the each tissue incorporating at least one of density of the each tissue and composition of the each tissue.

7. The method of claim 1, further comprising modeling a joint attenuation response of at least one known tissue at the first and the second radiation energy.

8. The method of claim 7, wherein the joint attenuation response is modeled based upon at least one of density of the each tissue, composition of the each tissue, and attenuation characteristics of tissue components.

9. The method of claim 7, further comprising classifying the one or more tissues in the first or the at least one second image based, at least in part, upon a plurality of joint attenuation response models for one or more known tissues.

10. The method of claim 1, further comprising modeling one or more extreme conditions based, at least in part, upon the joint attenuation characteristics.

11. The method of claim 1, further comprising designing the spectral filter for the desired tissue based, at least in part, on noise in the first image and the at least one second image.

12. The method of claim 1, wherein determining the joint attenuation characteristics comprises applying local spatial variational analysis, wherein the local spatial variational analysis is determined through at least one of regional sampling, anatomical and data priors, and training from pre-classified data.

13. An image processing apparatus comprising:
a data acquisition unit configured to obtain a first image of an anatomical object corresponding to a first radiation energy, and at least one second image of the anatomical object corresponding to at least one second radiation energy, wherein the anatomical object comprises one or more tissues and wherein the at least one second radiation energy is distinct from the first radiation energy; and
a processor configured to:
determine joint attenuation characteristics at said one or more tissues at the first radiation energy and the at least one second radiation energy;
design a spectral filter for at least one desired tissue from the one or more tissues based at least in part on the joint attenuation characteristics and a mixing proportion of a plurality of constituents of the at least one desired tissue; and
selectively filter using the spectral filter, attenuation values due to the at least one desired tissue from a reference image to generate an enhanced image, wherein the reference image is one of the first image or the at least one second image.

14. The apparatus of claim 13, wherein the processor is further configured to generate a mutual information map between the first image and the at least one second image based on attenuation values of voxels in the first image and attenuation values of corresponding voxels in the at least one second image.

15. The apparatus of claim 13, further comprising:
a radiation source configured to generate radiations at various energy levels;
a radiation detector array capable of receiving radiations at various energy levels through the anatomical object; and
a controller operatively coupled to the radiation source and the radiation detector to control the radiation source and the radiation detector.

16. The apparatus of claim 13, further comprising an operator console configured to receive input for controlling the apparatus.

17. The apparatus of claim 13, further comprising an output device configured to display at least one of input user command, the first image, the at least one second image and the enhanced image.

* * * * *